(12) United States Patent
Witvliet et al.

(10) Patent No.: US 11,311,614 B2
(45) Date of Patent: Apr. 26, 2022

(54) VACCINES CONTAINING SWINE PATHOGENS FOR ASSOCIATED NON-MIXED USE

(71) Applicant: Intervet Inc., Madison, NJ (US)

(72) Inventors: Maarten Hendrik Witvliet, Oostrum (NL); Erwin van den Born, Wageningen (NL); Melanie Sno, Budapest (HU); Antonius Arnoldus Christiaan Jacobs, Kessel (NL)

(73) Assignee: Intervet Inc., Madison, NJ (US)

( * ) Notice: Subject to any disclaimer, the term of this patent is extended or adjusted under 35 U.S.C. 154(b) by 0 days.

(21) Appl. No.: 16/604,188

(22) PCT Filed: Apr. 12, 2018

(86) PCT No.: PCT/EP2018/059389
§ 371 (c)(1),
(2) Date: Oct. 10, 2019

(87) PCT Pub. No.: WO2018/189290
PCT Pub. Date: Oct. 18, 2018

(65) Prior Publication Data
US 2020/0046825 A1 Feb. 13, 2020

(30) Foreign Application Priority Data
Apr. 13, 2017 (EP) .................................... 17166590

(51) Int. Cl.
*A61K 39/02* (2006.01)
*A61K 39/00* (2006.01)
*A61K 39/12* (2006.01)

(52) U.S. Cl.
CPC .......... *A61K 39/12* (2013.01); *A61K 39/0241* (2013.01); *A61K 39/105* (2013.01); *A61K 2039/521* (2013.01); *A61K 2039/5254* (2013.01); *A61K 2039/54* (2013.01); *A61K 2039/545* (2013.01); *A61K 2039/552* (2013.01)

(58) Field of Classification Search
None
See application file for complete search history.

(56) References Cited

U.S. PATENT DOCUMENTS

| 8,728,487 | B2 | 5/2014 | Wu et al. | |
| 2006/0193874 | A1* | 8/2006 | Jones | A61P 1/04 424/234.1 |
| 2013/0266602 | A1 | 3/2013 | Nitzel | |
| 2013/0266603 | A1 | 10/2013 | Nitzel | |
| 2016/0303218 | A1* | 10/2016 | Jacobs | A61P 31/04 |
| 2019/0209673 | A1* | 7/2019 | Nitzel | A61K 39/295 |
| 2020/0023128 | A1* | 1/2020 | Fachinger | A61M 5/2033 |

FOREIGN PATENT DOCUMENTS

| JP | 2016539132 A | 12/2016 |
| JP | 2017501985 A | 1/2017 |
| RU | 2166327 C2 | 5/2001 |
| WO | 9636356 A1 | 11/1996 |
| WO | 2006074986 A2 | 7/2006 |
| WO | 2007028823 A1 | 3/2007 |
| WO | 2007094893 A2 | 8/2007 |
| WO | 2008076915 A2 | 6/2008 |
| WO | 2009127684 A1 | 10/2009 |
| WO | 2014/048955 A1 | 4/2014 |
| WO | 2015082465 A1 | 6/2015 |

OTHER PUBLICATIONS

Fraile et al. Canadian J. Vet. Res. 73: 308-312, 2009.*
Himmler et al. Database Biosis online, Biosciences Information Service, Tieraerztliche Umsshau, 61-65, 2013—abstract.*
Gillespie et al. J. Vet. Intern. Med. 23: 1151-1163, 2009.*
Jeong et al. J. Swine Health Prod. 24(3): 130-141, May and Jun. 2016.*
Boehringer Imgelheim, Flex Family(TM) Customized Control Mixing Guide—CAS XP-002773133, 2016, 2 pages.
European search report for application 17166590.4 dated Sep. 8, 2017, 2 pages, European search report for application 17166590.4 dated Sep. 8, 2017, 2 pages.
International search report, dated Jun. 18, 2018, International search report for PCT/EP 2018/059389 dated Jun. 18, 2918, 5 pages.
Tzika, E,D, et al, Field efficacy study of a novel ready-to-use vaccine against mycoplasma hyopneumoniae and porcine circovirus type 2 in a Greek farm, Porcine Health Management, 2015, pp. 1-7, vol. 1 No. 15.
Weibel, H et al, Effi cacy of simultaneous vaccination with Enterisol@ Ileitis and Ingelvac® CircoFLEXTM in a Swiss breeding farm, Schweizer Archiv für Tierheilkunde, 2012, pp. 45-450, vol. 154 No. 10.
Boehringer Ingelheim Vetmedica, Inc., The FLEX Family of swine vaccines puts you in control, FlexFamily Customized Control, 2013, 1-14, N/A.

(Continued)

*Primary Examiner* — Sarvamangala Devi

(74) *Attorney, Agent, or Firm* — Michael D. Davis

(57) ABSTRACT

The present invention pertains to a combination of a first vaccine comprising non-replicating immunogen of porcine circo virus type 2 (PCV2) and non-replicating immunogen of *Mycoplasma hyopneumoniae*, and a second vaccine comprising live attenuated porcine reproductive and respiratory syndrome (PRRS) virus, for use in prophylactically treating an animal against an infection with porcine circovirus type 2, an infection with *Mycoplasma hyopneumoniae* and an infection with PRRS virus, by associated non-mixed administration of the first vaccine and the second vaccine to the animal. The invention also pertains to a kit-of-parts comprising the first and second vaccine and to a method of protecting an animal against such infections using these vaccines.

9 Claims, 2 Drawing Sheets

(56) References Cited

OTHER PUBLICATIONS

Figure 2:
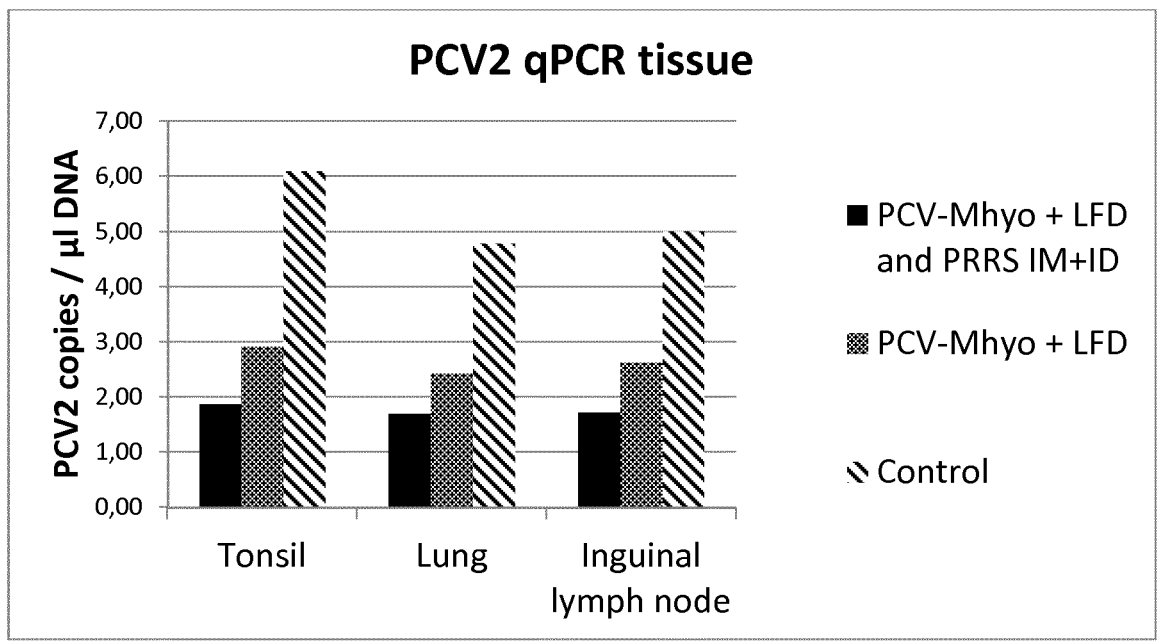

Boehringer Ingelheim, The ultimate in customization for control of three respiratory diseases in swine: PCV2, M. hyo and PRRS, 3FLEX® webpage, 2016, 1-2 [The Wayback Machine—https://web.archive.org/web/20161006163501/http://www.bi-vetmedica.com:80/species/swine/products/flex_vaccines/3flex.html], N/A.

Eichmeyer, M. et al., Efficacy of Ingelvac® PRRS MLV when rehydrated with a combination of Ingelvac MycoFLEX® and Ingelvac CircoFLEX®, Boehringer Ingelheim Vetmedica, Inc., 2010, 175 + 1-3, N/A.

Eichmeyer, Marc A. et al., Evaluation of Ingelvac® 3FLEX: Demonstration of efficacy for the mixture of Ingelvac® PRRS MLV when rehydrated with Ingelvac CircoFLEX® and Ingelvac MycoFLEX®, Boehringer Ingelheim Vetmedica, Inc., 2009, 1-6, N/A.

Fangman, T. et al., Serologic response of weaned pigs vaccinated with 3FLEX™ is similar to pigs vaccinated with Ingelvac® CircoFLEX-MycoFLEX™aod Ingelvac® PRRS MLV in separate injections, Leman Swine Conference, 2011, 262, Abstract.

\* cited by examiner

FIGURE 1

VACCINES CONTAINING SWINE PATHOGENS FOR ASSOCIATED NON-MIXED USE

CROSS-REFERENCE TO RELATED APPLICATIONS

This application is a national stage entry under 35 U.S.C. § 371 of PCT/EP2018/059389, filed on Apr. 12, 2018, which claims priority to EP Application 17166590.4, filed on Apr. 13, 2017, the content of PCT/EP2018/059389 is hereby incorporated by reference in its entirety.

GENERAL FIELD OF THE INVENTION

The invention in general pertains to the field of swine health. Swine are prone to many pathogenic micro-organisms. Control of infection is commonly done by farm and feed management, treatment with pharmaceuticals such as anti-viral drugs and antibiotics, or prophylactic treatment using vaccines. In particular, the invention pertains to vaccines against porcine circo virus type 2 (PCV2 or PCV-2), *Mycoplasma hyopneumoniae*, porcine reproductive and respiratory syndrome (PRRS) virus and optionally *Lawsonia intracellularis*, and to a method of protecting an animal against such infections using such vaccines.

BACKGROUND OF THE INVENTION

PCV-2 is linked to the post-weaning multisystemic wasting syndrome (PMWS) observed in young pigs. This disease was encountered for the first time in Canada in 1991. The clinical signs and pathology were first published in 1996, and include progressive wasting, dyspnea, tachypnea, and occasionally icterus and jaundice.

Nayar et al., Can. Vet. J. Volume 38, June 1997 detected porcine circo virus in pigs with clinical symptoms of PMWS and concluded that a PCV, other than the known PCV recognized as a natural inhabitant of PK-15 cells, could be linked to PMWS. Later publications (Hamel et al., J. Virol., 72(6), 5262-5267, 1998; Meehan et al., J. Gen. Virol., 79, 2171-2179, 1998) confirmed these findings, and it was proposed (Meehan et al., supra) to refer to the new pathogenic PCV as PCV-2, whereas the original PK-15 cell culture isolate (Tischer et al., Nature 295, 64-66, 1982), should be referred to as PCV-1. PCV-2 is a small (17-22 nm) icosahedral non-enveloped virus containing a circular single stranded DNA genome. The length of the PCV-2 genome is about 1768 bp. PCV-2 isolates originating from different regions in the world seem to be closely related to each other and display about 95 to 99% nucleotide sequence identities (Fenaux et al., J. Clin. Micorbiol., 38(7), 2494-2503, 2000). ORF2 of PCV encodes the capsid protein of the virus. The ORF2 gene of PCV 2 encodes a protein of about 233 amino acids. The ORF 2 gene of all PCV-2 isolates share 91-100% nucleotide sequence identity and 90-100% deduced amino acid sequence identity.

*Mycoplasma hyopneumoniae* (Mhyo) is a species of bacteria known to cause the disease Porcine Enzootic Pneumonia, a highly contagious and chronic disease affecting pigs. Mhyo is small in size (400-1200 nm), has a small genome (893-920 kilo-base pairs (kb)) and lacks a cell wall. Mhyo attaches to the cilia of epithelial cells in the lungs of swine. They cause cilia to stop beating, clumping and loss of cilia, eventually leading to epithelial cell death. This is the source of the lesions found in the lungs of pigs with porcine enzootic pneumonia. This damage impedes normal ciliary clearance and often secondary infections develop. This causes a significant reduction in the growing weight of the animals. Losses in the U.S.A. have been previously estimated to be up to 1 billion dollars per annum. Porcine enzootic pneumonia is endemic worldwide and Mhyo is present in almost every pig herd. The immune response induced by the presence of Mhyo in pigs is slow and ineffective. Treatment of this disease is therefore of the utmost importance but is limited to antibiotics, which are currently only partly effective as they do not completely remove the infection. Vaccines have been found to reduce the severity of the disease but do not completely prevent the disease from occurring in infected pigs.

PRRS virus was first reported in 1987 in North America and Central Europe. PRRS virus is a small, enveloped RNA virus. It contains a single-stranded, positive-sense, RNA genome with a size of approximately 15 kilobases. The genome contains nine open reading frames. The virus is a member of the genus Arterivirus, family Arteriviridae, order Nidovirales. The two prototype strains of PRRSV are the North American strain, VR-2332, and the European strain, the Lelystad virus (LV). The European and North American PRRSV strains cause similar clinical symptoms. Recently a highly pathogenic strain of the North American genotype emerged in China. This strain, HP-PRRSV, is more virulent than all other strains, and causes great losses in Asian countries. Clinical signs include reproductive failure in sows such as abortions and giving birth to stillborn or mummified foetuses, and cyanosis of the ear and vulva. In neonatal pigs, the disease causes respiratory distress, with increased susceptibility to respiratory infections such as Glässer's disease.

*Lawsonia intracellularis* causes proliferative enteropathy, also known as ileitis, which is a common enteric disease of post-weaned pigs worldwide. The characteristic lesion is a proliferation of immature enterocytes in the ileal intestinal crypts; these cells usually contain the causative bacteria within their apical cytoplasm. At autopsy, histologic lesions can be confirmed as *Lawsonia*-positive by visualization of 1.5-2.5 µm long, vibrioid shaped bacteria especially in enterocytes, but also often within macrophages located in the lamina propria between crypts, and in mesenteric lymph nodes. Clearance of the bacteria from the enterocytes leads to resolution of the associated proliferative lesions, indicating a direct local effect of the bacteria on the crypts. The presence of *Lawsonia intracellularis* in these lesions has been demonstrated using PCR, both in animals manifesting disease as in animals manifesting only subclinical infection. Clinical cases are usually present in the grower-finisher period; in some older finisher pigs an acute hemorrhagic form has been recorded.

Vaccines against the above identified pathogens are commonly known. A conventional vaccine to prophylactically treat animals, in particular pigs, against an infection with PCV 2, may be based on whole inactivated PCV-2 virus as (non-replicating) immunogen. Also, in the art it has been shown that the ORF2 encoded capsid protein (e.g. when recombinantly expressed) is suitable as a subunit immunogen of porcine circo virus type 2 for use in an adequate vaccine. This can be understood since this subunit in a circulatory system, shows up the same way as the virus itself (it forms virus-like particles), essentially differing only in the fact that the DNA and non-structural proteins are not present inside the capsid. In the art several vaccines against PCV2 are commercially available. Porcilis® PCV (available from MSD Animal Health, Boxmeer, The Netherlands) is a vaccine for protection of pigs against porcine circo virus type 2, for use in pigs from three weeks and older. When given as a two-shot (two dose) vaccine, the duration of immunity (DOI) is 22 weeks, almost completely covering the fattening period of pigs. Ingelvac CircoFlex® (available from Boehringer Ingelheim, Ingelheim) is a vaccine for protection of pigs against porcine circo virus type 2, for use in pigs from two weeks and older. It is registered as a one-shot (one dose) vaccine only. Circovac® (available from Merial, Lyon, France) is a vaccine for protection of pigs against porcine circo virus type 2, for use in pigs three weeks and older. Suvaxyn® PCV (available from Zoetis, Capelle a/d IJssel, The Netherlands) is a vaccine for protection of pigs against porcine circo virus type 2, for use in pigs from three weeks and older. Other PCV2 vaccines are described for example in WO2007/028823, WO 2007/094893 and WO2008/076915.

Regarding *Mycoplasma hyopneumoniae* many commercial vaccines exist and these are routinely used in the majority of commercial swine farming operations. Generally these vaccines comprise non-replicating immunogens such as subunit proteins and/or bacterins (i.e. a composition comprising killed bacteria, either as whole cells, (partly) lysed, homogenised, French pressed, a combination of this or comprising the killed bacteria in another form as long as the composition is derived from a killed bacterial culture) which are typically administered by parenteral injection. Some examples are: RespiSure® (Zoetis), Ingelvac® M. hyo, and MycoFLEX® (Boehringer Ingelheim), Hyoresp® (Merial), Stellamune® *Mycoplasma* (Elanco Animal Health), Fostera® PCV MH (Zoetis) and M+Pac® and Porcilis® Mhyo (both available from MSD Animal Health).

Regarding PRRS virus, although inactivated virus vaccines have been described and are commercially available, modified live vaccines (MLV vaccines) comprising either the European type (type I) or the North American type (type II) in live attenuated form, are the primary immunological tool for its control. Several vaccines are commercially available in the art. Porcilis® PRRS (available from MSD Animal Health, Boxmeer, The Netherlands) is a vaccine comprising live attenuated PRRS virus type I and is registered to reduce infection (viraemia) caused by infection with PRRS virus. Ingelvac PRRS® MLV (available from Boehringer Ingelheim, Ingelheim) is a vaccine that aids in the reduction of disease caused by PRRS virus and which vaccine provides cross protection against strains of different types. Fostera® PRRS (available from Zoeitis, Florham Park, N.J., USA) is also a MLV vaccine and is registered for protection against both the respiratory and reproductive forms of disease caused by PRRS virus. Yet another PRRS MLV vaccine is PrimePac PRRS (type II) available from Merck Animal Health, Madison, N.J., USA. Other PRRS vaccines are described for example in WO2006/074986, U.S. Pat. No. 8,728,487 and WO2014/048955.

Vaccines to combat *Lawsonia intracellularis* by inducing active protection are commercially available and described in the art. These vaccines are available under the tradenames Enterisol® Ileitis (Boehringer Ingelheim Vetmedica, USA) which is a live attenuated vaccine, and Porcilis® Ileitis (Merck Animal Health, USA) which is a vaccine comprising non-replicating immunogen of *Lawsonia intracellularis* in the form of a bacterin.

OBJECT OF THE INVENTION

There is a continuous need for convenient, safe and efficacious means for the management of swine health. In particular, there is a need for convenient, safe and efficacious vaccines that can be used for prophylactic treatment of a swine against an infection with porcine circovirus type 2, an infection with *Mycoplasma hyopneumoniae* and an infection with PRRS virus.

SUMMARY OF THE INVENTION

In order to meet the object of the invention a combination of a first vaccine and a second vaccine has been devised, the first vaccine comprising non-replicating immunogen of porcine circo virus type 2 (PCV2) and non-replicating immunogen of *Mycoplasma hyopneumoniae*, and the second vaccine comprising live attenuated porcine reproductive and respiratory syndrome (PRRS) virus, wherein the combination is for use in prophylactically treating an animal against an infection with porcine circovirus type 2, an infection with *Mycoplasma hyopneumoniae* and an infection with PRRS virus, by associated non-mixed administration of the first vaccine and the second vaccine to the animal.

Although for each pathogen mentioned here above vaccines are known and commercially available, there is no combination of vaccines available for associated non-mixed administration, which combination of vaccines provides the required efficacy and at the same time is safe for use in animals, in particular young animals. As is commonly known, not all combinations of antigens contemplated or suggested may lead to a safe and effective combination vaccine. Correspondingly, the associated non mixed use of vaccines, also referred to as concurrent administration, may cause interactions leading to safety issues or diminished response to the individual immunogens as present in the vaccines. In the case of live vaccines, diminished replication of the vaccine strain may appear. Interference between different immunogens can result from various immunological events such as antigenic competition. Antigenic competition describes the phenomenon that an immune response to a particular immunogen (also referred to as antigen) may be diminished in the presence of other immunogens, compared to when the same immunogen is given alone.

As proof for the commonly known problem of interference of vaccines even when administered without being mixed, is the guideline as published on 18 Jul. 2013 by the Committee for Medicinal Products for Veterinary Use (CVMP) of the European Medicines Agency (EMA) titled "*Guideline on the requirements for combined vaccines and associations of immunological veterinary medicinal products (IVMPs)*" (EMA/CVMP/IWP/594618/2010). In section 5.1 it is stated that "The basis for association of IVMPs should be a demonstration of acceptable safety and absence of serious interference between the IVMPs involved. If the safety profile for the association is less favourable than that established for the separate products, the association should be justified by an appropriate benefit-risk analysis, where the benefits of the association clearly outweigh the risks of reduced safety. In such situations, the SPCs of the separate products should be amended to reflect the safety profile due to associated use of the IVMPs. If some level of interference between the products in the association leads to a reduction of efficacy, the association of the IVMPs needs further justification on a case by case basis. It should also be noted that changes that have an impact on the production or composition of any of the concerned IVMPs will also require re-evaluation of the compatibility of the association."

Moreover, in particular for any combined administration with live PRRS virus: If anything, it is expected that there will be a negative impact on efficacy towards the other immunogens since PRRS virus is commonly known to be immune suppressive. See for example Can J Vet Res. 2012 October; 76(4):255-60: *"Suppression of immune responses in pigs by nonstructural protein 1 of porcine reproductive and respiratory syndrome virus."* by Zhou Y1, Bai J, Li Y, Wang X, Wang X, Jiang P.

All in all, it is commonly known that combined vaccination against multiple pathogens is not straightforward and requires experimentation to determine safety and efficacy, in particular when the combined vaccination involves a live PRRS virus.

It is noted that the present invention also pertains to a kit-of-parts comprising a first vaccine comprising non-replicating immunogen of porcine circo virus type 2 (PCV2) and non-replicating immunogen of *Mycoplasma hyopneumoniae*, and separately a second vaccine comprising live attenuated PRRS virus, for use in prophylactically treating an animal against an infection with porcine circovirus type 2, an infection with *Mycoplasma hyopneumoniae* and an infection with PRRS virus by associated non-mixed administration of the first vaccine and the second vaccine to the animal.

The invention also pertains to a method of prophylactically treating an animal against an infection with porcine circovirus type 2 (PCV2), an infection with *Mycoplasma hyopneumoniae* and an infection with PRRS virus by associated non-mixed administration of a first vaccine comprising non-replicating immunogen of porcine circo virus type 2 and non-replicating immunogen of *Mycoplasma hyopneumoniae*, and a second vaccine comprising live attenuated PRRS virus.

The invention also pertains to a vaccine comprising non-replicating immunogen of porcine circo virus type 2 (PCV2) and non-replicating immunogen of *Mycoplasma hyopneumoniae*, for use in prophylactically treating an animal against an infection with porcine circo virus type 2, an infection with *Mycoplasma hyopneumoniae* and an infection with PRRS virus, by associated non-mixed administration of the vaccine with another vaccine comprising live attenuated porcine reproductive and respiratory syndrome (PRRS) virus to the animal. Correspondingly, the invention pertains to a vaccine comprising live attenuated porcine reproductive and respiratory syndrome (PRRS) virus, for use in prophylactically treating an animal against an infection with porcine circo virus type 2, an infection with *Mycoplasma hyopneumoniae* and an infection with PRRS virus, by associated non-mixed administration of the vaccine with another vaccine comprising non-replicating immunogen of porcine circo virus type 2 (PCV2) and non-replicating immunogen of *Mycoplasma hyopneumoniae* to the animal. Each of the particular embodiments as described here beneath in the section "Embodiments of the invention" can be combined with these two vaccines for use according to the present invention.

It is noted that in a vaccine the immunogen (also called antigen) is typically combined with a pharmaceutically acceptable carrier, i.e. a biocompatible medium, viz. a medium that after administration does not induce significant adverse reactions in the subject animal, capable of presenting the immunogen to the immune system of the host animal after administration of the vaccine, such as a liquid containing water and/or any other biocompatible solvent or a solid carrier such as commonly used to obtain freeze-dried vaccines (based on sugars and/or proteins), optionally comprising immunostimulating agents (adjuvants), which upon administration to the animal induces an immune response for treating an animal against an infection with a wild-type micro-organism, i.e. for aiding in preventing, ameliorating or curing such infection or a disorder arising therefrom. Optionally other substances such as stabilisers, viscosity modifiers or other components are added depending on the intended use or required properties of the vaccine.

BRIEF DESCRIPTION OF THE DRAWINGS

Figure 1:
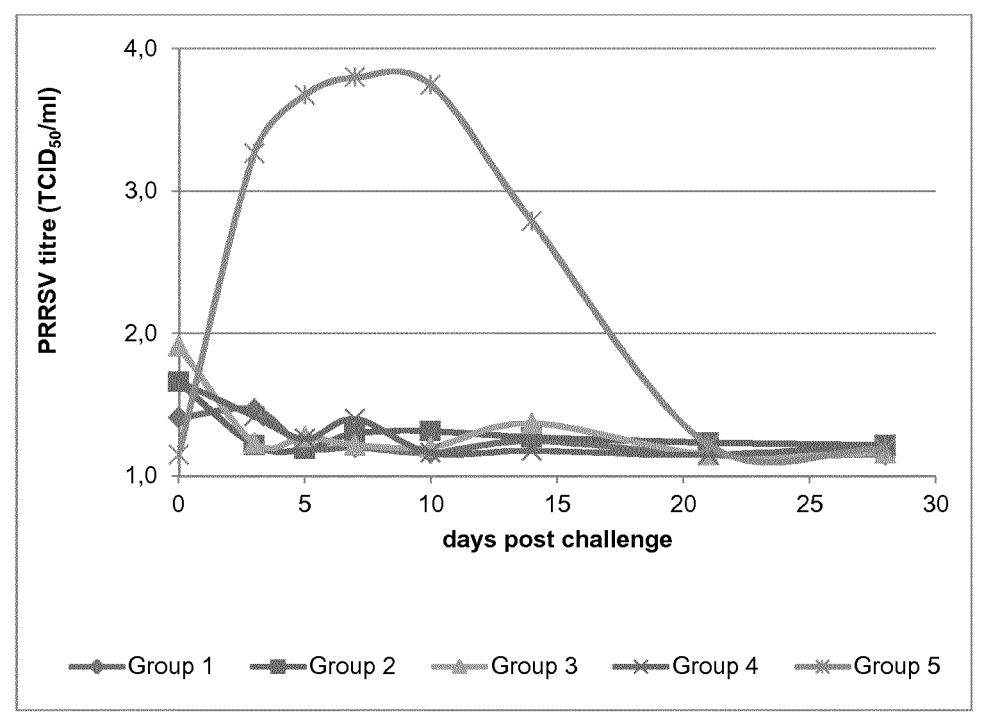

FIG. 1 depicts the titer of PRRSV versus the number of days post challenge for various vaccination experiments.

FIG. 2 depicts the number of PCV2 virus copies in various organs after different treatments.

DETAILED DESCRIPTION OF THE INVENTION

Definitions

A vaccine is a pharmaceutical composition that is safe to administer to a subject animal, and is able to induce protective immunity in that animal against a pathogenic micro-organism, i.e. to induce a successful prophylactic treatment as defined here below.

Non-replicating immunogen of a pathogen is any substance or compound corresponding to the pathogen, other than the live replicating pathogen as a whole (either in wild type of attenuated form), against which pathogen an immunological response is to be elicited, such that the corresponding virulent pathogen or one or more of its virulence factors will be recognized by the host's immune system as a result of this immune response and are ultimately at least partly neutralized. Typical examples of non-replicating immunogens are killed whole pathogens (which term includes these pathogens in lysed form) and subunits of these pathogens such as capsid proteins, surface expressed molecules (for example recombinantly expressed proteins or lipopolysaccharides) and excreted molecules such as toxins.

A live attenuated pathogen is a viable, replication competent form of the pathogen having reduced virulence. The process of attenuation takes an infectious pathogen and alters it so that it becomes harmless or less virulent, typically by either multiple passages of the pathogen through cell systems or by genetically modifying the pathogen.

Prophylactic treatment against an infection with a pathogen is aiding in preventing, ameliorating or curing an infection with that pathogen or a disorder arising from that infection, resulting from a post treatment challenge with the pathogenic pathogen, in particular to reduce its load in the host after such challenge and optionally to aid in preventing or ameliorating one or more clinical manifestations resulting from the post treatment infection with the pathogen.

Associated non-mixed administration of vaccines, also referred to as concurrent administration, is the administration of these vaccines separately, thus not mixed before administration, to the target animal, but within a time frame such that immunological interference may occur, typically within 24 hours. Examples of associated non-mixed use are the simultaneous administration at separate application sites in the target animal, and the administration at the same or separate application sites but at different times, typically separated by 1-6 hours.

Simultaneous administration of vaccines means the administration at exactly the same time or at least within a time frame of 1 hour, preferably within 55, 50, 45, 40, 35, 30, 25, 20, 19, 18, 17, 16, 15, 14, 13, 12, 11, 10, 9, 8, 7, 6, 5, 4, 3, 2 minutes or even a time frame of 1 minute.

Single dose administration of a vaccine for use in prophylactically treatment means that in order to arrive at protective immunity, the vaccination does not need to be boosted with a second administration of the vaccine. In a two-shot regime, the first (prime) vaccination is typically boosted within 6 weeks from the first administration, commonly within 3 or even 2 weeks from the first administration, and only after the second (boost) administration protective immunity, i.e. a successful prophylactic treatment as defined here above, may be obtained.

EMBODIMENTS OF THE INVENTION

In an embodiment of the combination of a first and a second vaccine for use according to the invention, the associated non-mixed administration occurs simultaneously. This embodiment has the advantage that an animal needs to be handled only once for applying both the vaccines.

In another embodiment of the present combination of vaccines, the second vaccine is administered into the dermis of the animal. Such administration of at least the PRRS vaccine has shown to be safe and efficacious while at the same time being less stressful for the animal when compared to intramuscular administration. Regarding administration into the dermis (also referred to as intradermal administration), although such administration is often carried out using a needle-less vaccination device such as the IDAL® vaccinator (available from MSD Animal Health, Boxmeer, The Netherlands), "intradermal" administration per se should not be equated with "needle-less" administration. The World health Organization in its Aug. 27, 2009 paper titled "Intradermal Delivery of Vaccines; A review of the literature and the potential for development for use in low- and middle-income countries" indeed clearly indicates that "needle-less" vaccination does not necessarily mean "intradermal" vaccination (see Table 1, Page 3 of the review). Only when a needle-less device is "configured for intradermal vaccination", then a vaccine may indeed be delivered (at least partly) into the dermis. Otherwise the vaccine may be delivered subcutaneous or intramuscularly in its entirety.

In yet another embodiment of the combination of the first and a second, the first vaccine comprises non-replicating immunogen of *Lawsonia intracellularis*. In this embodiment the novel combination of vaccines is capable of providing protection against four major swine pathogens by using just one vaccination protocol. The immunogen of *Lawsonia intracellularis* in an embodiment is combined with the immunogen of PCV2 and *Mycoplasma hyopneumoniae* within 24 hours before administration, preferably within 6 hours before administration. Combining the antigens right before administration provides more freedom to choose the excipients since long-term stability, although known for many pharmaceutical compositions, even for combination vaccines including PCV2 ORF2 antigen (for example Porcilis® PCV M Hyo, available from MSD Animal Health), as such is known, might still not be straightforward to achieve, at least not for any and all pharmaceutically acceptable carrier compositions. In a further embodiment the immunogen of *Lawsonia intracellularis* is added to the vaccine in the form of a composition comprising freeze-dried killed whole cells of *Lawsonia intracellularis*.

In still another embodiment of the novel combination of a first and a second vaccine, the first and second vaccine are administered by a single dose. It was found that a single dose administration led to an effective vaccination against all pathogens. This provides for a very convenient and economical way to protect animals against these pathogens.

In another embodiment the non-replicating immunogen is recombinantly expressed protein encoded by the ORF2 gene of PCV2, for example expressed by baculovirus as known in the art. This recombinant protein has proven to be suitable for application in the present invention. In particular, the ORF2 protein can be expressed in a baculovirus expression system such as described in WO2007/028823, WO 2007/094893 or WO2008/076915.

In again another embodiment, the non-replicating immunogen of *Mycoplasma hyopneumoniae* comprise killed whole *Mycoplasma hyopneumoniae*. Such Mhyo antigen is relatively easy to produce and has a good track record of efficacy in the everyday swine industry practice.

The invention will now be explained in more detailed, using the following examples.

EXAMPLES

Study 1: Safety and Protection Against PRRSv Challenge by the Associated Non-Mixed Use of Porcilis® PCV MHyo with *Lawsonia* Immunogen Reconstituted Therein, and Porcilis® PRRS.

This study was performed to evaluate the safety and efficacy of Porcilis® PRRS in associated non-mixed use with freeze-dried killed whole cells of *Lawsonia intracellularis* (also referred to as "*Lawsonia* freeze-dried") reconstituted in Porcilis® PCV M Hyo. The study was performed with sixty PRRSV antibody negative piglets, evenly distributed over 5 groups of 12 piglets each. Four groups were vaccinated at the age of 3 weeks with either 2 mL of Porcilis® PRRS intramuscularly (IM; groups 1 and 3) or 0.2 mL of Porcilis® PRRS intradermally (ID; groups 2 and 4). Piglets from groups 1 and 2 were vaccinated with *Lawsonia* freeze-dried reconstituted in Porcilis® PCV M Hyo (2 mL; IM) within a couple of minutes after receiving the PRRS vaccine. Piglets in group 5 (also 12 piglets) were not vaccinated and served as non-vaccinated challenge controls. Four weeks after vaccination all piglets were challenged by the intranasal (IN) route using a heterologous virulent PRRSV Type 1 strain (Isolate 2).

After challenge infection, the following parameters were measured: clinical signs, rectal temperatures, and PRRSV viremia and serology.

No clinical signs related to PRRSV challenge were observed in any of the groups. Rectal temperatures were measured for 12 days starting on one day before challenge until 10 days post challenge. No significant differences were observed between any of vaccinated groups. The rectal temperatures of all PRRS vaccinated groups were lower compared to the control group at several time points post challenge. There was neither a statistical significant difference between IM or ID vaccinated groups, nor between groups treated with Porcilis® PRRS alone or Porcilis PRRS in combination with *Lawsonia* freeze-dried reconstituted in Porcilis® PCV M Hyo.

A significant reduction of PRRSV viremia compared to the non-vaccinated controls was shown if piglets were vaccinated with Porcilis® PRRS and if piglets were vaccinated with Porcilis® PRRS combined with vaccination of *Lawsonia* freeze-dried reconstituted in Porcilis® PCV M Hyo (FIG. 1). No significant difference was detected between single and non-mixed associated use of Porcilis® PRRS administrated via the IM or ID route.

All vaccinated groups showed an anti-PRRSV antibody titer 4 weeks post vaccination at the day of challenge, while the control group did not. Four weeks post challenge all groups show an anti-PRRSV antibody titer and the titer in the vaccinated groups is higher than on the day of challenge. No statistical significant difference was detected between single and non-mixed associated use of Porcilis® PRRS administered via the IM or ID route.

In conclusion, the concurrent administration of *Lawsonia* freeze-dried reconstituted in Porcilis® PCV M Hyo had no negative effect on Porcilis® PRRS vaccination via either the IM or ID route. It was unexpected that the associated use of the triple *Lawsonia*-PCV-Mhyo vaccine had no negative effect at all on the efficacy of the PRRS vaccine (see study 5).

Study 2: PCV2 Efficacy Study of the Associated Non-Mixed Use of Porcilis® PCV MHyo with *Lawsonia* immunogen reconstituted therein, and Porcilis® PRRS.

A total of 45 piglets with low to moderate maternally derived PCV2 antibody titers (<5.5 log$_2$), no PCV2 viral load and no PRRSV antibody titers were allotted to 3 treatment groups: 3 groups of 15 piglets each. The piglets were vaccinated once at 3 weeks of age. The piglets of group 1 and 2 were vaccinated with *Lawsonia* FD dissolved in Porcilis PCV M Hyo, both as a single dose (intramuscular route; IM) and the piglets from group 1 were also vaccinated at about the same time with Porcilis PRRS (via both the intramuscular and intradermal route; IM and ID). The animals from group 3 remained unvaccinated (control).

At 5 weeks of age (2 weeks post vaccination), each animal was challenge infected using wild-type PCV2 challenge virus applied intranasally. 21 days following challenge, all animals were necropsied and inguinal lymph node, tonsil and lung were sampled for the detection of PCV2.

Serum samples were taken at the time of vaccination, one day before challenge, at 2 and 3 weeks after challenge. Samples were examined for PCV2 antibodies and viral nucleic acid. Faecal and nasal swabs taken one day before challenge, at 2 and 3 weeks after challenge were examined for viral nucleic acid.

Serology showed that both vaccinated groups developed anti-PCV2 antibodies to a comparable level (6 log 2) at the time of challenge, whereas the antibodies in the control group had declined significantly. After challenge, antibodies in the vaccinated groups rose to about 13 log 2 measured 3 weeks post challenge. In the control group the level was 5 log 2 at that time. After challenge, viral nucleic acid could be detected in the control animals in the serum, nasal and faecal swabs. The level was substantially lower in the vaccinated animals. In the faecal samples, the animals vaccinated with both vaccines simultaneously had no detectable levels of viral nucleic acid, suggesting that this group was best protected against the PCV2 challenge. This surprising finding of a possible improved protection was confirmed by the qPCR measurements in the tissue, as can be seen in FIG. 2 (representing the PCV2 copies found in Tonsils, Lung and Inguinal lymph node respectively going from left to right). The lowest values for viral load were consistently found in the animals that received both vaccines (left column), even lower than for the animals that received the commercial PCV vaccine Porcilis® PCV M Hyo (middle columns), which were still considerably lower than control (right columns).

Study 3: Efficacy of Freeze-Dried *Lawsonia* Reconstituted in Porcilis® PCV M Hyo Used Concurrently with Porcilis® PRRS in Pigs, Against *Lawsonia* Challenge.

For this study seventy-five 3-week-old piglets, divided over three groups, were used.

Group 1 was vaccinated with freeze-dried *Lawsonia* antigen reconstituted in Porcilis® PCV M Hyo (2 ml IM) administered at the same time (within 1 hour) with Porcilis® PRRS (2 ml IM+0.2 ml ID), group 2 was vaccinated with freeze-dried *Lawsonia* antigen reconstituted in Porcilis PCV M Hyo (2 ml IM) and group 3 was left as unvaccinated controls. At 7 w of age (4 weeks after vaccination) all pigs were challenged orally with homogenized *Lawsonia* infected intestinal mucosa. After challenge the pigs were daily observed for clinical signs. At regular times before and after challenge serum blood (for serology) and faeces (for qPCR) samples were collected. Three weeks after challenge the pigs were euthanized and post-mortem examined. The intestines were checked macroscopically for *Lawsonia intracellularis* infection and ileum samples were collected for qPCR and (immuno-)histological scoring.

On day of vaccination most pigs were either seronegative to *Lawsonia* whereas the others had a low to moderate antibody titer. After the vaccination the titer of groups 1 and 2 showed a similar increase in the antibody titre, whereas the controls showed a slight decrease and remained at a low level. On the day of vaccination the pigs had low to moderate maternally derived PCV antibody titers. After the vaccination the PCV antibody titer of groups 1 and 2 showed a similar increase whereas the controls showed a decrease of maternal antibodies. On day of vaccination the pigs were seronegative to Mhyo and PRRSv. After vaccination groups 1 and 2 showed a similar antibody response to Mhyo whereas the control group 3 remained seronegative until the end of the trial. Group 1 responded to the PRRS vaccination whereas groups 2 and 3 remained seronegative until challenge.

The results for the different parameters after *Lawsonia* challenge are summarized in Table 1 below (PCR data in log$_{10}$ pg DNA/μl on day 21 post challenge).

TABLE 1

| Group | PCR on faeces | PCR on mucosa | Macroscopic ileum scores | Immunohistological ileum scores |
| --- | --- | --- | --- | --- |
| 1 | 0.00 | 0.22 | 40 | 0.6 |
| 2 | 0.60 | 0.41 | 84 | 0.8 |
| 3 | 1.72 | 1.15 | 161 | 5.0 |

From the results it can be concluded that *Lawsonia* freeze-dried antigen dissolved in Porcilis® PCV M Hyo administered concurrently with Porcilis® PRRS (group 1), induced significant protection against *Lawsonia* infection 4 w after vaccination. This was demonstrated by a significant reduction in shedding, infection (qPCR ileum mucosa), macroscopic ileum lesion scores as well as microscopic ileum lesion scores. No negative influence of Porcilis® PRRS on the *Lawsonia* efficacy was observed. On the contrary, the associated mixed use group tended to be better for the above mentioned parameters.

Study 4: Efficacy of Associated Non-Mixed Use of Porcilis® PCV M Hyo with *Lawsonia* Freeze-Dried Reconstituted Therein, with Porcilis® PRRS in SPF Piglets at Three Weeks of Age Against *M. Hyopneumoniae* Challenge Infection 4 Weeks after Vaccination.

Hundred pigs from a *M. hyopneumoniae* and PRRS virus free herd, 3 weeks of age, were used for this study in groups of 25 animals each. One group was vaccinated IM with Porcilis® PCV M Hyo+*Lawsonia* freeze-dried and concurrently with Porcilis® PRRS (IM+ID; see here above); one group was vaccinated with Porcilis® PCV M Hyo and at about the same time (within 1 hour) with Porcilis® PRRS (IM+ID) and one group with Porcilis® PCV M Hyo; the fourth group was not vaccinated and served as challenge control. Four weeks after vaccination all animals were infected with a virulent *M. hyopneumoniae* strain and three weeks later all animals were post-mortem investigated for lung lesions.

All animals were serologically negative for *M. hyopneumoniae* at vaccination and non-vaccinated animals remained serologically negative until challenge infection. Vaccinated groups showed similar serological responses against *M. hyopneumoniae* four weeks post vaccination and three weeks post challenge infection.

A significant reduction in lesion score was observed for all vaccinated groups compared to non-vaccinated animals. Porcilis® PCV M Hyo+*Lawsonia* freeze-dried, vaccinated concurrently with Porcilis® PRRS had a reduction of 90%, Porcilis® PCV M Hyo vaccinated concurrently with Porcilis® PRRS had a reduction of 95%. Porcilis® PCV M Hyo induced 100% reduction in median *M. hyopneumoniae* lesions. The differences between the vaccinated groups were not significant.

It can be concluded that associated non-mixed use of Porcilis® PCV M Hyo alone or in combination with freeze-dried *Lawsonia* antigen and Porcilis® PRRS is efficacious in reducing *M. hyopneumoniae*-induced lung lesions.

Study 5: The Effect of the Use of an Inactivated PCV Vaccine on the Efficacy of a Live PRRS Vaccine.

In this experiment the effect of mixing a first vaccine containing non-replicating immunogen of porcine circo virus type 2 (CircoFLEX, Boehringer Ingelheim) and a second vaccine comprising live attenuated porcine reproductive and respiratory syndrome virus (Ingelvac PRRS, Boehringer Ingelheim) was examined. Since the survival of the live PRRS virus is the main critical parameter when mixing these two vaccines, the survival of the PRRS virus after an incubation of 1, 2 and 4 hours was examined.

On day −1, MA104 cells were seeded at $10^5$ cells/ml and put in wells at 225 µl per well. These cells were kept at 37° C. in air with a 5% carbon dioxide content. On day 0 Ingelvac PRRS was prediluted in PBS to a titer of 5.3 log 10 TCID50/ml. This mixture was either diluted with PBS (control) or diluted with CircoFLEX (two different batches) to a final titer of 5.0 log 10 TCID50/ml. The final mixtures were incubated at room temperature for 1, 2 and 4 hours to mimic practical circumstances in a stable when vaccinating with a freshly mixed combination vaccine. After this, 25 µl of each of the incubated mixtures was incubated in the MA 104 cells for 7 days at 37° C. and 5% carbon dioxide to grow the PRRS virus. At day 7 the PRRS virus was read out. The data are given here below in Table 2.

TABLE 2

PRRS titer in 10 log TCID50/ml after incubation with PCV

| Sample | Start | 1 h incubation | 2 h incubation | 4 h incubation |
|---|---|---|---|---|
| PRRS control | 5.0 | 4.90 | 4.80 | 4.64 |
| PRRS + PCV batch 1 | 5.0 | 3.90 | 3.90 | 3.15 |
| PRRS + PCV batch 2 | 5.0 | 3.85 | 3.55 | 3.55 |

As can be seen from the table, the PRRS virus loses viability by the short incubation with the PCV vaccine at room temperature. Vaccine efficacy will be negatively influenced by a loss of vaccine titer.

The invention claimed is:

1. A method of prophylactically treating an animal against a porcine circo virus type 2 (PCV2) infection, a *Mycoplasma hyopneumoniae* infection, and a porcine reproductive and respiratory syndrome (PRRS) virus infection by concurrent associated non-mixed administration of a first vaccine and a second vaccine to the animal,
   wherein the first vaccine comprises a non-replicating immunogen of porcine circo virus type 2 and a non-replicating immunogen of *Mycoplasma hyopneumoniae*, and the second vaccine comprises a live attenuated porcine reproductive and respiratory syndrome virus (PRRS) vaccine and
   wherein the associated non-mixed administration occurs simultaneously and the first vaccine and the second vaccine are administered at separate application sites of the animal and wherein the associated non-mixed administration of the first vaccine and the second vaccine confers improved protection to the animal against the PCV2 infection when compared to the administration of the first vaccine alone in the absence of the concurrent non-mixed administration of the live attenuated PRRS vaccine.

2. The method of prophylactically treating the animal of claim 1, wherein the second vaccine is administered into the dermis of the animal.

3. The method of prophylactically treating the animal of claim 1, wherein the first vaccine further comprises a non-replicating immunogen of *Lawsonia intracellularis* which reconstitutes the first vaccine.

4. The method of prophylactically treating the animal of claim 3, wherein the non-replicating immunogen of *Lawsonia intracellularis* is added to the first vaccine within 24 hours before the associated non-mixed administration of the first vaccine.

5. The method of prophylactically treating the animal of claim 4, wherein the non-replicating immunogen of *Lawsonia intracellularis* comprises freeze-dried killed whole cells of *Lawsonia intracellularis*.

6. The method of prophylactically treating the animal of claim 1, wherein the first vaccine and the second vaccine are administered by a single dose.

7. The method of prophylactically treating the animal of claim 1, wherein the non-replicating immunogen of PCV2 is a recombinantly expressed protein encoded by the ORF2 gene of the PCV2.

8. The method of prophylactically treating the animal of claim 7, wherein the non-replicating immunogen of PCV2 is baculovirus expressed protein of the PCV2.

9. The method of prophylactically treating the animal of claim 1, wherein the non-replicating immunogen of *Mycoplasma hyopneumoniae* comprises killed whole *Mycoplasma hyopneumoniae*.

* * * * *